(12) United States Patent
Bille et al.

(10) Patent No.: US 6,579,282 B2
(45) Date of Patent: Jun. 17, 2003

(54) DEVICE AND METHOD FOR CREATING A CORNEAL REFERENCE FOR AN EYETRACKER

(75) Inventors: Josef Bille, Heidelberg (DE); Frieder Loesel, Heidelberg (DE)

(73) Assignee: 20/10 Perfect Vision Optische Geraete GmbH (DE)

( * ) Notice: Subject to any disclaimer, the term of this patent is extended or adjusted under 35 U.S.C. 154(b) by 0 days.

(21) Appl. No.: 09/842,354

(22) Filed: Apr. 25, 2001

(65) Prior Publication Data

US 2002/0161356 A1 Oct. 31, 2002

(51) Int. Cl.[7] .................................................. A61F 9/01
(52) U.S. Cl. ............................................. 606/5; 351/210
(58) Field of Search .......................... 606/4–6; 607/89; 351/209, 210

(56) References Cited

U.S. PATENT DOCUMENTS

| | | |
|---|---|---|
| 4,772,115 A | 9/1988 | Gersten et al. |
| 4,848,340 A | 7/1989 | Bille et al. |
| 4,905,711 A | 3/1990 | Bennett et al. |
| 4,988,348 A | 1/1991 | Bille |
| 4,994,058 A | 2/1991 | Raven et al. |
| 5,062,702 A | 11/1991 | Bille |
| 5,108,412 A | 4/1992 | Krumeich et al. |
| 5,336,215 A | 8/1994 | Hsueh et al. |
| 5,865,830 A * | 2/1999 | Parel et al. ............... 606/5 |
| 5,984,916 A | 11/1999 | Lai |

* cited by examiner

Primary Examiner—Andrew M. Dolinar
(74) Attorney, Agent, or Firm—Nydegger & Associates

(57) ABSTRACT

A device and method for increasing the accuracy of an ocular laser procedure by detecting and compensating for small eye movements includes the establishment of a corneal reference plane. To create the corneal reference plane, a laser beam is first used to photoablate stromal tissue at three different locations in the cornea. Bubbles that are created upon photoablation define the plane and can be imaged to determine the position of the plane as the eye moves. A pair of cameras and a processor are provided to image the cornea and triangulate the position of the reference plane. The updated position of the corneal reference plane is then used to guide the path of the laser beam during the course of the ocular procedure.

17 Claims, 2 Drawing Sheets

DEVICE AND METHOD FOR CREATING A CORNEAL REFERENCE FOR AN EYETRACKER

FIELD OF THE INVENTION

The present invention pertains generally to ophthalmic devices and procedures. More particularly, the present invention pertains to devices and methods that are useful for tracking the movement of an eye during a diagnosis of the eye or during a corrective procedure such as corneal laser surgery. The present invention is particularly, but not exclusively, useful for tracking rotational movements of the eye.

BACKGROUND OF THE INVENTION

The use of lasers is now almost commonplace in a variety of ophthalmic applications, including the diagnosis and treatment of ocular diseases, as well as the diagnosis and correction of optical deficiencies. As an example, corneal reshaping procedures using lasers, such as the well known LASIK procedure, are now widely available. When used, these procedures often obviate the need for glasses and/or contact lenses. In all of these procedures, the laser is chosen as the tool of choice because of the ability of the laser to be focused on extremely small amounts of ocular material. In addition, the ability of the laser to be guided to prescribed locations within the eye with precision and reliability has enabled a whole new class of ophthalmic procedures that require nothing short of pinpoint accuracy. Unfortunately, movements of the eye relative to the laser source can undermine the accuracy of the laser and reduce the efficacy of ocular laser procedures.

Movements of the eye can be classified broadly into voluntary and involuntary movements. Voluntary movements can often be almost completely eliminated in most patients by instructing the patient to concentrate (i.e. fixate) on a small light source. Still, a small percentage of patients, such as infants and some toddlers, are unable to follow instructions, and as such, voluntary movements in these patients can have adverse effects on a laser operation unless the movements are either compensated for or eliminated. Although involuntary eye movements cannot be remedied by instruction they must also be somehow controlled. Included in the involuntary eye movements are movements due to the patient's pulse or breathing. These involuntary eye movements, however, generally occur at a relatively low frequency (e.g. 1 Hz). Additionally, even psychotic eye movements, such as can occur when a patient is startled, generally occur at a frequency in the range of only approximately 50 Hz. Moreover, psychotic eye movements don't generally occur during eye fixation. A typical laser procedure, however, can be accomplished relatively quickly (e.g. several m Sec). Nevertheless, involuntary eye movement must either be compensated for, or effectively eliminated.

One way to reduce or effectively eliminate the adverse consequence of either voluntary or involuntary eye movements is to restrain the eye. In this regard, several devices have been disclosed in the art that mechanically apply a pressure to the eye for the purpose of restraining the eye. Generally, this pressure is applied to the surface of the eye (i.e. the sclera, limbus or cornea). It is to be appreciated, however, that eye restraint systems suffer from several drawbacks. First, the restraint device may need to be positioned along a desirable laser path. If so, the restraint device can interfere with the laser procedure. Further, the pressure applied to the eye can be sufficient to change the shape of the eye and, thereby, complicating the effort to focus the laser with high degrees of accuracy. Importantly, the pressure applied to the eye is often uncomfortable to the patient and can result in post-operative pain and scarring. Finally, the pressure can cause damage to the eye by increasing the intra-ocular pressure of the eye to dangerous levels.

Important for the present invention is the technique used to sense eye movement. Heretofore, several techniques for sensing eye movement have been disclosed. One way to track the eye is to find a pre-existing optical feature of the eye and track the optical feature. One such technique is to follow the displacement of one or more of the purkinje projections. Other devices use the visible contrast of the eye to track the eye. For example, one system tracks the edge between the iris and the pupil, and another system tracks the edge between the iris and the sclera. Another disclosed system uses the overall contrast of the eye to track movement with the use of photodetectors in an all analog system. However, the use of pre-existing landmarks requires custom system calibration for each patient (i.e. the surgeon must define and find the landmark (or at least verify that the system has found the correct pre-existing landmark) within the initial system coordinates. Further, eye contrasts vary from patient to patient, leading to scattered results.

Several benefits accrue to systems that establish a reference mark on the eye and then use the created reference mark to track eye movement. One advantage, as alluded to above, is consistency from eye to eye. In one respect, the contrast and spatial resolution of the created reference mark can be controlled. Also, and importantly for the present invention, the shape and location of the mark can be controlled. For example, in U.S. Pat. No. 4,848,340 entitled "Eyetracker and Method of Use", a reference mark created by cutting a mark onto the surface of the cornea is described.

A general knowledge of the anatomy of the cornea of an eye is helpful for appreciating the problems that must be confronted when creating reference marks within the stroma of the cornea. The cornea comprises various layers of tissue which are structurally distinct. In order, going in a posterior direction from outside the eye toward the inside of the eye, the various layers in a cornea are: an epithelial layer, Bowman's membrane, the stroma, Decimet's membrane, and an endothelial layer. Of these various layers, the stroma is the most extensive and is generally around four hundred microns thick.

In detail, the stroma of the eye is comprised of identifiable and distinguishable layers of lamellae. Each of these layers of lamellae in the stroma is generally dome-shaped, like the cornea itself, and they extend across a circular area having a diameter of approximately six millimeters. Unlike the layer that a particular lamella is in, each lamella extends through a shorter distance of only about one tenth to one and one half millimeters. Thus, each layer includes several lamellae. Importantly, each lamella includes many fibrils which, within the lamella, are substantially parallel to each other. The fibrils in one lamella, however, are not generally parallel to the fibrils in other lamellae. This is so between lamellae in the same layer, as well as between lamellae in different layers. Finally, it is to be noted that, in a direction perpendicular to the layer, the individual lamella are only about two microns thick.

Within the general structure described above, there are at least three important factors concerning the stroma that are of interest insofar as the creation of a reference mark in the stroma of the cornea is concerned. The first of these factors is structural, and it is of interest here because there is a significant anisotropy in the stroma. Specifically, the strength of tissue within a lamella is approximately fifty times the strength that is provided by the adhesive tissue that holds the layers of lamella together. Thus, much less energy is required to separate one layer of lamella from another layer (i.e. peel them apart), than would be required to cut through a lamella.

The second factor is somewhat related to the first, and involves the stromal tissue response to photoablation. Specifically, for a given energy level in a photoablative laser beam, the bubble that is created by photoablation in the stronger lamella tissue will be noticeably smaller than a bubble created between layers of lamellae. Conversely, for a given energy level, a larger bubble can be created at the interface between layers of lamellae. Thus the present invention recognizes that it is preferable to create large bubbles at the interface between lamellae using relatively low laser energies for photoablation. The large bubbles create a reference mark that is easy to image, while the use of a low energy laser for photoablation minimizes collateral damage to the stroma.

In the context of creating a corneal flap for a LASIK type procedure, a method for finding an interface between layers of lamellae for photoablating using a wavefront analyzer and an ellipsometer was disclosed in copending U.S. patent application No. 09/783,665, filed on Feb. 14, 2001, by Billie and entitled "Method for Separating Lamellae." As such, the contents of copending application Ser. No. 09/783,665 are herein incorporated by reference.

In light of the above, it is an object of the present invention to provide devices and methods suitable for establishing a corneal reference plane that can be used to track the movement of the eye during a subsequent ocular procedure. It is another object of the present invention to provide methods for creating a suitable corneal reference mark while minimizing collateral damage to the cornea. It is yet another object of the present invention to provide a method for tracking rotational movements of the eye by creating a corneal reference plane and tracking the tilt of the reference plane. Still another object of the present invention is to provide a device and method for creating corneal reference marks so quickly (i.e. all reference marks created in about 1.5 mSec.) that involuntary eye movements do not interfere with the creation of the reference mark. Yet another object of the present invention is to provide a method for tracking the movements of an eye during an ophthalmic procedure which is easy to use, relatively simple to implement, and comparatively cost effective.

SUMMARY OF THE PREFERRED EMBODIMENTS

The present invention is directed to a device and method for tracking the movements of an eye during an ocular laser procedure and compensating for those eye movements to increase the accuracy of the laser procedure. In accordance with the present invention, three marks defining a corneal reference plane are first created for use in observing the position of the eye. Specifically, a laser beam is used to photoablate tissue at three different locations within the stroma of the cornea and thereby establish a reference mark at each of the three locations.

For each mark, a plurality of points is photoablated, creating a bubble at each point. Preferably, each mark includes approximately twelve bubbles. For the present invention, the bubbles are preferably arranged in the shape of an annular segment. It is also preferable that each bubble within a mark, as well as each mark, be created within the stroma at approximately the same predetermined depth from the anterior surface of the cornea. For this purpose, the eyetracker device of the present invention includes a wavefront detector to establish the position of the anterior surface of the cornea. Once the position of the anterior surface of the cornea is established, the laser beam can be focused within the stromal tissue of the cornea, at a predetermined depth from the anterior surface.

As indicated above, for each mark, approximately twelve points will be photoablated, resulting in approximately 12 bubbles. For the present invention, each of the bubbles will preferably be formed at an interface between two layers of lamellae. This allows for relatively large bubbles to be created with relatively low laser energies and consequently, minimal collateral damage to the stromal tissue. For this purpose, the eyetracker device can include a wavefront detector and an ellipsometer. In detail, the laser can be focused on a first point at the location of the mark to photoablate tissue and produce a first bubble. Next, the wavefront detector can be used to measure the size of the first bubble. The size of the first bubble can then be compared to a reference bubble (e.g. a bubble of 15 $\mu$m diameter) to determine whether the first point lies on an interface between layers of lamellae. Specifically, if the first bubble is larger than the reference bubble, the first point is determined to lie on an interface between layers of lamellae.

For the case where the bubble comparison shows that the first point lies on an interface between layers of lamellae, then the next point selected for photodisruption is selected to be at approximately the same depth from the anterior surface of the cornea as the first point. On the other hand, if the bubble comparison shows that the first point does not lie on an interface between layers of lamellae, then the second point is selected at a slightly different depth from the anterior surface of the cornea than the first point. This process is repeated until a point on an interface between layers of lamellae is found. Once an interface is found, the ellipsometer can be used to ensure that all the bubbles created for a mark are photoablated on a single interface. Thus, the ellipsometer can be used to ensure the entire reference mark is created at a constant depth from the anterior surface of the cornea.

Once the reference marks are established in the cornea, the reference marks can be used to track the eye during an ocular laser procedure such as LASIK. By tracking the eye during the procedure, the system can then compensate for any eye movements, thereby increasing the accuracy of the procedure. During the ocular procedure, the focal point of the laser beam will be directed within the cornea with reference to the corneal reference plane. To accomplish this, the path of the laser focal point required for the ocular laser procedure is first prescribed for the eye at rest. The optical axis of the eye in combination with the anterior surface of the eye can provide a reference system for establishing this prescribed path. Next, the three reference marks are established in the cornea at known locations relative to the reference system (i.e. the optical axis of the eye in combination with the anterior surface of the eye). To accomplish this, the patient is asked to fixate on a light source, aligning the optical axis of the eye with a known axis, while the reference marks are created. Once the prescribed path for the ocular laser procedure and the corneal reference plane are established relative to the reference system (i.e. the optical axis of the eye in combination with the anterior surface of the eye), the relationship between the prescribed path and the corneal reference plane can be calculated.

During the ocular laser procedure, movement of the eye will cause the corneal reference plane to move to a new position. In accordance with the present invention, the movement can be monitored using two cameras and a confocal detector. Specifically, movement of the corneal reference plane along the optical axis (i.e. the z-axis) can be measured with the confocal detector, while off-axis movement of the corneal reference plane (i.e. movement in the x-y direction) can be measured by the pair of cameras. In accordance with the present invention, the measurements from the confocal detector and the images from the cameras can be input into a processor equipped with digital imaging software to triangulate the position of the reference plane. Once the new position of the corneal reference plane is obtained, the focal point of the laser beam can be directed (relative to the new corneal reference position) along the prescribed path through the cornea.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
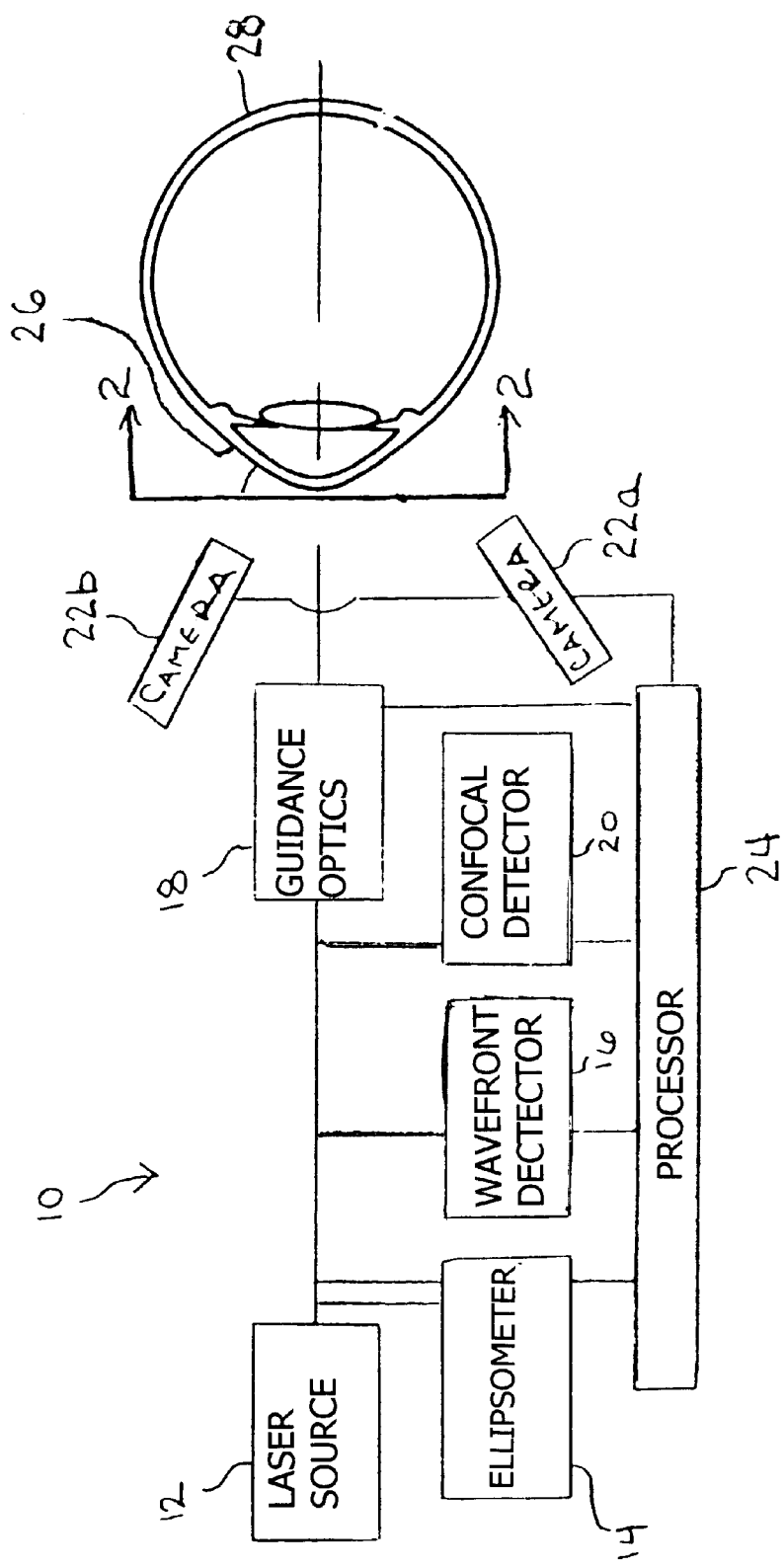
FIG. 1 is a schematic diagram showing the operative components of a device in accordance with the present invention.

Referring initially to FIG. 1, a device in accordance with the present invention is shown schematically and generally designated 10. As shown, the device 10 includes a laser source 12 which, preferably, has a photoablation mode in which the laser source 12 generates a continuous train of ultra-short pulses, with each pulse having a pulse duration of approximately one picosecond. Specifically, it is necessary that each pulse have an energy level that is above the threshold necessary for the photoablation of stromal tissue (i.e. above approximately one and one half microjoules per ten micron diameter spot size). The device 10 also includes an ellipsometer 14 that is capable of determining the birefringent properties within stromal tissue. For the purposes of the present invention, a suitable type of ellipsometer is disclosed and claimed in U.S. Pat. No. 5,822,035, which issued to Bille for an invention entitled "Ellipsometer." Further, FIG. 1 shows that the device 10 includes a wavefront detector 16, such as a Hartmann-Shack sensor, which is capable of modeling a wavefront. Additionally, as shown, the device 10 includes guidance optics 18 that are capable of steering and focusing a laser beam onto predetermined focal points. Also shown, the device 10 includes a confocal detector 20 and a pair of cameras 22a,b. A processor 24, which is preferably a dedicated computer, is also provided to process data and control the other components of the device 10. As detailed more fully below, these components cooperate in combination to establish a reference plane within the cornea 26 of the eye 28 that can be used to track the movement of the eye 28 during a subsequent ocular procedure.

Figure 2:
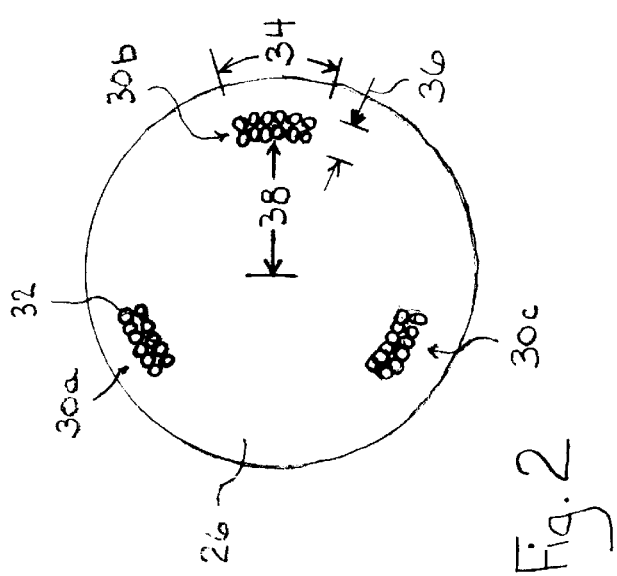
FIG. 2 is a plan view of the cornea as seen along line 2—2 in FIG. 1 showing a corneal reference plane that has been established by photoablating three reference marks in the stroma.

In accordance with the present invention, corneal reference marks delineating a reference plane such as the marks 30a–c shown in FIG. 2 are first created for use in observing the position of the eye. Specifically, a laser beam is used to photoablate tissue at three different locations within the stroma of the cornea 26 and thereby establish a reference mark 30 at each of the three locations. As shown, for each mark 30, a plurality of points is photoablated, creating a bubble 32 at each point. Preferably, each mark 30 includes approximately twelve bubbles 32. For the present invention, the bubbles 32 are preferably arranged in the shape of an annular segment. A suitable mark 30, in accordance with the present invention, has a segment length 34 of approximately 150 $\mu$m, a segment width 36 of approximately 50 $\mu$m, and is positioned at a distance 38 of approximately 5 mm from the center of the cornea 26.

It is also preferable that each bubble 32 within a mark 30, as well as each mark 30, be created within the stroma at approximately the same predetermined depth from the anterior surface of the cornea 26. For this purpose, the wavefront detector 16 can be used to establish the position of the anterior surface of the cornea 26 using techniques well known in the pertinent art. Once the position of the anterior surface of the cornea 26 is established, the laser beam can be focused within the stromal tissue of the cornea 26, at a predetermined depth from the anterior surface.

Figure 3:
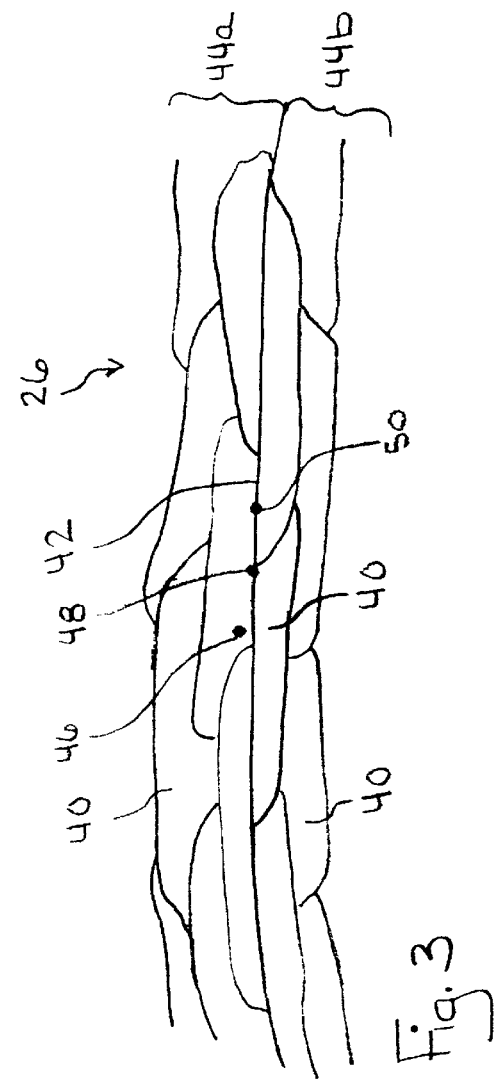
FIG. 3 is a cross sectional view of layers of lamella in the cornea of an eye.

Referring now to FIG. 3, a plurality of lamellae 40 constituting a portion of the stroma of the cornea 26 is shown. An interface 42 between two layers of lamellae 44a and 44b is further shown in FIG. 3. As indicated above, and shown in FIG. 2, for each mark 30, approximately twelve points will be photoablated, resulting in approximately twelve bubbles 32. By cross referencing FIGS. 2 and 3, it is to be appreciated that each of the bubbles 32 will preferably be formed at an interface 42 between two layers of lamellae 44. This allows for relatively large bubbles 32 to be created with relatively low laser energies and consequently, minimal collateral damage to the stromal tissue of the cornea 26.

To position the bubbles 32 on an interface 42, the device 10 uses the wavefront detector 16 and the ellipsometer 14. In detail, a pulsed laser can be focused on a first point within the stroma of the cornea 26. Although the first point is chosen at the location of the mark 30 and at a predetermined depth from the anterior surface of the cornea 26, the first point may or may not lie on an interface 42.

Consider the case where the first point does not lie on the interface 42. Point 46, shown in FIG. 3, is one such point. Upon photoablation at point 46, a bubble 32 (not shown in FIG. 3) will result. Next, the wavefront detector 16 can be used to measure the size of the first bubble 32. The size of the first bubble 32 can then be compared to a reference bubble using the wavefront detector 16 and the processor 24 to determine whether the first point (i.e. point 46) lies on an interface 42 between layers of lamellae 44.

Continuing with the example, since point 46 lies within a lamella 40 and not on an interface 42, the bubble 32 produced will be smaller than the reference bubble and the processor 24 will determine that point 46 does not lie on an interface 42. As such, the second point is selected to be at a slightly different depth from the anterior surface of the cornea 26 than the first point. This process is repeated until an interface 42 between layers of lamellae 44 is found. Thus, eventually a point on the interface 42 such as point 48 will be found. It is to be appreciated that the interface 42 may be found with the first point. For points on the interface 42, the bubble 32 will be the same size or larger than the reference bubble.

Once a point on the interface 42 is found and photoablated, then the next point selected for photodisruption is selected to be at approximately the same depth from the anterior surface of the cornea 26 as the first point. For example, after the photoablation of exemplary point 48, the bubble 32 produced will be compared to the reference bubble and a determination made that point 48 lies on an interface 42. As such, the next point selected for photoablation will be selected at the same depth, such as exemplary point 50.

Once an interface 42 is found, the ellipsometer 14 can be used to verify that subsequent photoablation occurs on the same interface 42. This verification can be used to ensure the all the bubbles 32 of a mark 30 are created on the same interface 42. Specifically, advantage can be taken of the fact that from layer to layer of lamellae 44 there will be a birefringent change that is manifested as a change in phase of about one half degree. Thus, the detection of a birefringent change will indicate a change from one layer of lamellae 44 to another.

Once the reference marks 30a–c are established in the cornea 26, the reference marks 30 can be used to track the eye 28 during a laser procedure such as LASIK. By tracking the eye 28 during the procedure, the device 10 can compensate for movement of the eye 28, thereby increasing the accuracy of the procedure. During the ocular procedure, the focal point of the laser beam will be directed within the cornea with reference to the corneal reference plane defined by the reference marks 30. To accomplish this, the path of the laser focal point required for the ocular laser procedure is first prescribed for the eye 28 at rest. The optical axis of the eye 28 in combination with the anterior surface of the eye 28 can provide a reference system for establishing this prescribe path. Next, the three reference marks 30 are established in the cornea 26 at known locations relative to the reference system (i.e. the optical axis of the eye 28 in combination with the anterior surface of the eye 28). To accomplish this, the patient is asked to fixate on a light source, aligning the optical axis of the eye 28 with a known axis, while the reference marks 30 are created. Once the prescribe path for the ocular laser procedure and the corneal reference plane are established relative to the reference system (i.e. the optical axis of the eye 28 in combination with the anterior surface of the eye 28), the relationship between the prescribed path and the corneal reference plane can be calculated.

During the ocular laser procedure, movement of the eye 28 will cause the corneal reference plane to move to a new position. In accordance with the present invention, the movement can be monitored using the cameras 22a,b and the confocal detector 20. Specifically, movement of the corneal reference plane along the optical axis (i.e. the z-axis) can be measured with the confocal detector 20, while off-axis movement of the corneal reference plane (i.e. movement in the x-y direction) can be measured by the cameras 22a,b. In accordance with the present invention, the measurements from the confocal detector 20 and the images from the cameras 22a,b can be input into the processor 24 where digital imaging software can be used to triangulate the position of the reference plane. Once the new position of the corneal reference plane is obtained, the focal point of the laser beam can be directed (relative to the new corneal reference position) along the prescribed path through the cornea.

While the particular device and method for creating a corneal reference and tracking the eye as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A method for directing a laser beam to a target during an ocular laser procedure while compensating for eye movement, said method comprising the steps of:

using a laser beam to photoablate tissue at three different locations in the stroma of the cornea to produce a reference mark at each said location wherein each said reference mark is established by photoablating a plurality of points at each said location to create a bubble at each said point;

identifying a corneal reference plane using said three reference marks;

calculating the position of said target relative to said corneal reference plane; and monitoring movements of said corneal reference plane to direct said laser beam to said target.

2. A method as recited in claim 1 wherein said first reference mark is established by photoablating approximately twelve points at each said location.

3. A method as recited in claim 1 further comprising the steps of:

using a wavefront detector to determine the position of the anterior surface of the cornea; and establishing each said mark at approximately the same predetermined depth from said anterior surface of the cornea.

4. A method as recited in claim 1 further comprising the steps of:

focusing a laser at a first point within a first said location to photoablate tissue at said first point and produce a first bubble;

measuring the size of said first bubble using a wavefront detector;

determining whether said first point lies on an interface between layers of lamellae by comparing said size of said first bubble to a reference bubble; and selecting a second point for photodisruption adjacent said first point, said second point selected to be at approximately the same depth from the anterior surface of the cornea as said first point when said first point has been determined to lie on an interface between layers of lamellae, and said second point selected to be at a slightly different depth from the anterior surface of the cornea than said first point when said first point has been determined to lie within a layer of lamellae.

5. A method as recited in claim 2 wherein said bubbles in said first reference mark are arranged in the shape of an annular segment.

6. A method as recited in claim 2 wherein said locations all lie on a ring, said ring surrounding the central portion of the cornea.

7. A system for directing a laser beam to a target during an ocular laser procedure while compensating for eye movement, said system comprising:

means for photoablating the stroma of the eye the produce reference marks at three different locations to define a corneal reference plane;

means for calculating the position of said target relative to said corneal reference plane; and means for monitoring movements of said corneal reference plane to direct said laser beam to said target, wherein said monitoring means comprises a plurality of cameras, each said camera for creating an image of said cornea, and a processor for comparing the images from each said camera to determine the position of each said reference mark.

8. A system as recited in claim 7 further comprising a means for tracking the movement of the eye along the visual axis.

9. A system as recited in claim 8 wherein said means for tracking the movement of the eye along the visual axis comprises a confocal detector.

10. A system as recited in claim 7 further comprising a wavefront detector to determine the size of bubbles formed in the stroma due to photoablation.

11. A system as recited in claim 7 further comprising an ellipsometer for measuring the birefringence of a path through the cornea, said measurement for maintaining the focal point of the laser on an interface between layers of lamellae during photoablation of each said reference mark.

12. A method for directing a laser beam to a target during an ocular laser procedure while compensating for eye movement, said method comprising the steps of:

photoablating the stroma of the eye at three different locations while the eye remains substantially in a first position to produce a reference mark at each said location wherein each said reference mark is established by photoablating a plurality of points at each said location to create a bubble at each said point, said reference marks for defining a corneal reference plane;

establishing the position of said target relative to said corneal reference plane;

determining the positions of said reference marks after the eye has moved to a second position;

calculating the position of said target when said eye is in said second position; and directing said laser beam to said target when said eye is in said second position.

13. A method as recited in claim 12 wherein said first reference mark is established by photoablating approximately twelve points.

14. A method as recited in claim 12 wherein the step of photoablating the stroma at three different locations to produce a reference mark at each said location includes the steps of:

using a wavefront detector to determine the position of the anterior surface of the cornea; and establishing each said mark at approximately the same predetermined depth from said anterior surface of the cornea.

15. A method as recited in claim 12 wherein the step of photoablating the stroma at three different locations to produce a reference mark at each said location includes the steps of:

focusing a laser at a first point within a first said location to photoablate tissue at said first point and produce a first bubble;

measuring the size of said first bubble using a wavefront detector;

determining whether said first point lies on an interface between layers of lamellae by comparing said size of said first bubble to a reference bubble; and selecting a second point for photodisruption adjacent said first point, said second point selected to be at approximately the same depth from the anterior surface of the cornea as said first point when said first point has been determined to lie on an interface between layers of lamellae, and said second point selected to be at a slightly different depth from the anterior surface of the cornea than said first point when said first point has been determined to lie within a layer of lamellae.

16. A method as recited in claim 13 wherein said bubbles in said first reference mark are arranged in the shape of an annular segment.

17. A method as recited in claim 12 wherein said step of determining the positions of said reference marks after the eye has moved to a second position includes the steps of:

imaging the cornea with a plurality of cameras; and comparing the images from each said camera to determine the position of each said reference mark.

* * * * *